(12) United States Patent
Leontis et al.

(10) Patent No.: US 8,129,516 B1
(45) Date of Patent: *Mar. 6, 2012

(54) RNA COMPLEXES FEATURING PARANEMIC BINDING, METHODS OF THEIR PRODUCTION AND SENSORS AND ANALYTICAL METHODS INVOLVING SAME

(75) Inventors: Neocles Leontis, Bowling Green, OH (US); Kirill A. Afonin, Goleta, CA (US)

(73) Assignee: Bowling Green State University, Bowling Green, OH (US)

( * ) Notice: Subject to any disclaimer, the term of this patent is extended or adjusted under 35 U.S.C. 154(b) by 213 days.

This patent is subject to a terminal disclaimer.

(21) Appl. No.: 12/291,697

(22) Filed: Nov. 13, 2008

Related U.S. Application Data (60) Provisional application No. 61/002,858, filed on Nov. 13, 2007.

(51) Int. Cl.
*C07H 21/00* (2006.01)
(52) U.S. Cl. .................. 536/24.5; 536/24.1; 536/24.31; 514/44
(58) Field of Classification Search ........................ None
See application file for complete search history.

(56) References Cited

OTHER PUBLICATIONS

Horiya et al. (Chem. Biol. 10: 645-654, 2003).*
Holeman et al. Folding Design 1998, vol. 3: 423-431.*

* cited by examiner

*Primary Examiner* — Kimberly Chong
(74) *Attorney, Agent, or Firm* — Marshall & Melhorn, LLC (57) ABSTRACT

The present invention pertains to the use of paranemic crossover motifs for RNA self-assembly, and the use of those self-assembled complexes to carry out analytical methods, and as a basis for the creation of sensors. The invention includes RNA monomeric units comprising an RNA having a binding domain that is adapted to self-assemble paranemically so as to form an RNA complex with another RNA, the binding domain of the RNA monomeric unit comprising an aptameric portion bound to a fluorophore. The invention also includes RNA complexes comprising a target RNA molecule and at least one of these monomeric units which self-assemble paranemically so as to form the RNA complex comprising an aptameric portion. The invention also includes derivatives of these complexes including aptamers, and analytical methods and devices using same.

12 Claims, 9 Drawing Sheets
(8 of 9 Drawing Sheet(s) Filed in Color)

Figure 1

Annotated structure of MG aptamer contained in an RNA complex of the present invention

Figure 2

Schematic representation of the assembled complex causing the enhancement of Malachite Green (MG) emission signal

```
3651MG    GGGAUCCCUCAUGGUAACGAAUGAUAGCUUUAUCCGACACCAUCCAUCCC
3651MGa   GGGAUCCCUCAUGGUAACGAAUGAUAGCUUUAUCCGACACCAUCCAUCCC
3651MGc   GGGAUCCCUCUUGGUAACGAAUGAUAGCUUUAUCCGACACCAUCCAUCCC

3652      GGGUAUGAGGGUGAAGUUCGCUUCAGGAUGGAUCCC
3652a     GGGUAUGAGGCUGAAGUUCGCUUCAGGAUGGAUCCC
3652c     GGGUAAGAGGGUGAAGUUCGCUUCAGGAUGGAUCCC
```

Figure 6
Sequences of all token RNA tested

SEQUENCE LISTING

```
<160> NUMBER OF SEQ ID NOS: 6

<210> SEQ ID NO 1
<211> LENGTH: 50
<212> TYPE: RNA
<213> ORGANISM: Artificial
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 1
gggaucccuc augguaacga augauagcuu uauccgacac cauccauccc              50

<210> SEQ ID NO 2
<211> LENGTH: 50
<212> TYPE: RNA
<213> ORGANISM: Artificial
```

-continued

```
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 2
gggaugccuc augguaacga augauagcuu uauccgacac cauccauccc                  50

<210> SEQ ID NO 3
<211> LENGTH: 50
<212> TYPE: RNA
<213> ORGANISM: Artificial
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 3
gggaucccuc uugguaacga augauagcuu uauccgacac cauccauccc                  50

<210> SEQ ID NO 4
<211> LENGTH: 36
<212> TYPE: RNA
<213> ORGANISM: Artificial
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 4
ggguaugagg gugaaguucg cuucaggaug gauccc                                 36

<210> SEQ ID NO 5
<211> LENGTH: 36
<212> TYPE: RNA
<213> ORGANISM: Artificial
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 5
ggguaugagg cugaaguucg cuucaggaug gauccc                                 36

<210> SEQ ID NO 6
<211> LENGTH: 36
<212> TYPE: RNA
<213> ORGANISM: Artificial
<220> FEATURE:
<223> OTHER INFORMATION: Fusion of 3-dimensional RNA motifs using
      3-dimensional computer modeling.  Some motifs are ubiquitous,
      however, the 4-way helical junction in our artificial constructs
      is from the so-called "hairpin ribozyme" of Satellite Tobacco
      Ringspot Virus.

<400> SEQUENCE: 6
ggguaagagg gugaaguucg cuucaggaug gauccc                                 36
```

RNA COMPLEXES FEATURING PARANEMIC BINDING, METHODS OF THEIR PRODUCTION AND SENSORS AND ANALYTICAL METHODS INVOLVING SAME

RELATED APPLICATION DATA

The present application claims the priority benefit of U.S. Provisional Patent Application Ser. No. 61/002,858, filed Nov. 13, 2007, which, along with the references referred to therein, is hereby incorporated herein by reference. The present application hereby incorporates by reference co-pending U.S. patent application Ser. No. 11/196,003, and the references referred to therein.

TECHNICAL FIELD

The present invention is in the fields of biochemistry and molecular biology, and relates to analytical methods and sensors in those fields.

BACKGROUND OF THE INVENTION

In the fields of biochemistry and molecular biology, it is often desirable to be able to prepare stable and reproducible molecular constructs that may serve as templates or reagents in analytical schemes designed to detect the presence of organic and biochemical analytes.

In biomimetic nanotechnology one aims to construct complex, nano-scale supramolecular structures from modular units using a "bottom-up" approach inspired by biological systems. The pre-formed modular units are designed to undergo controlled and reversible self-assembly without external manipulation of individual molecules.[1,2] This approach imitates the self-assembly of complex objects in biological systems, which produce large complex structures such as ribosomes and splicesomes from smaller modular structures by hierarchical folding and assembly.[3] Moreover, such biological structures are dynamic, comprise moving parts and successfully bind and release dissociable factors during functional cycles.

The use of RNA as a medium for nanotechnology, has been called "RNA tectonics" and involves three steps:[4,5] 1) Conceptual, modular design at the level of 3D structure using computer modeling techniques, 2) realization of the 3D design as the requisite supporting secondary structure and 3) detailed design of uniquely folding sequence.[2,6-8] Recent work in RNA nanotechnology has resulted in the design of artificial RNA units that assemble to form oriented filaments, closed complexes, and 2D arrays.[4,9-11] The programmed assembly of RNA monomers ("tecto-RNAs") requires specific tertiary interactions. These can be identified in atomic-resolution 3D structures or selected in vitro using SELEX methods.[12] "Loop-receptor" interactions, which form between specific hairpin or internal loops and cognate receptor motifs, comprise an important type of tertiary motif that occurs recurrently in large biological RNA molecules. They are sufficiently weak to be readily reversible and occur in all large biological RNA structures.[4,5,13] Loop-receptor interactions avoid plectonemic braiding of individual RNA stem-loops, which would entangle the interacting units and therefore require unfolding of secondary structure to form. Therefore they can be considered a simple form of paranemic binding motif. The diversity of artificial RNA self-assembling modules ("RNA tectons") is limited by the availability and specificity of receptor-loop motifs. Accordingly, alternate binding motifs that allow for more programmability, while maintaining similar geometries, are desirable.

It is desirable to be able to develop RNA as a medium for (1) exploring principles of supramolecular self-assembly and (2) achieving nano-scale molecular design and construction of complex cooperative assemblies capable of realizing diverse functions and practical applications.

There is also a need for biomolecules that can be used as stable electrophoresis markers and electron microscopy markers.

There also remains a need for RNA constructs with increased stability, and those that may be readily and reliably applied in analytical methods and devices by using conformational strategies to bind, isolate and detect target biomolecules.

In this regard, it is desirable to be able to efficiently produce biochemicals that may be used to bind, isolate and detect target RNA sequences though Watson-Crick interactions, and to be able to readily determine when such interactions have taken place for analytical purposes.

SUMMARY OF THE INVENTION

The present invention involves the use of paranemic crossover motifs for RNA self-assembly, and the use of those self-assembled complexes to carry out analytical methods, and as a basis for the creation of sensors.

DNA nanotechnology generally utilizes stably branched DNA molecules that are assembled with structurally well-defined cohesion methods, most usually sticky-end Watson-Crick basepairing.[14] This approach has been applied to construct regular 2D and 3D geometric molecular objects such as planar squares and triangles,[15] and polyhedra such as cubes[16] and truncated octahedra.[17] Linear 2D and 3D arrays have also been developed using double- and triple-crossover junctions, both based on stable Holliday junctions.[14,18,19] Recently, nano-mechanical devices have been developed such as stress gauges,[20] molecular switches,[21,22] and DNA walking devices.[23] Both single and double paranemic cohesions have been utilized to assemble large objects into 2D arrays.[24] The development of new cohesion motifs including paranemic cohesion has played an important role in the development of DNA nanotechnology. It has been suggested that paranemic DNA structures occur also in living systems, participating in genes committed to or undergoing copying processes during replication.[25]

Figure 1:
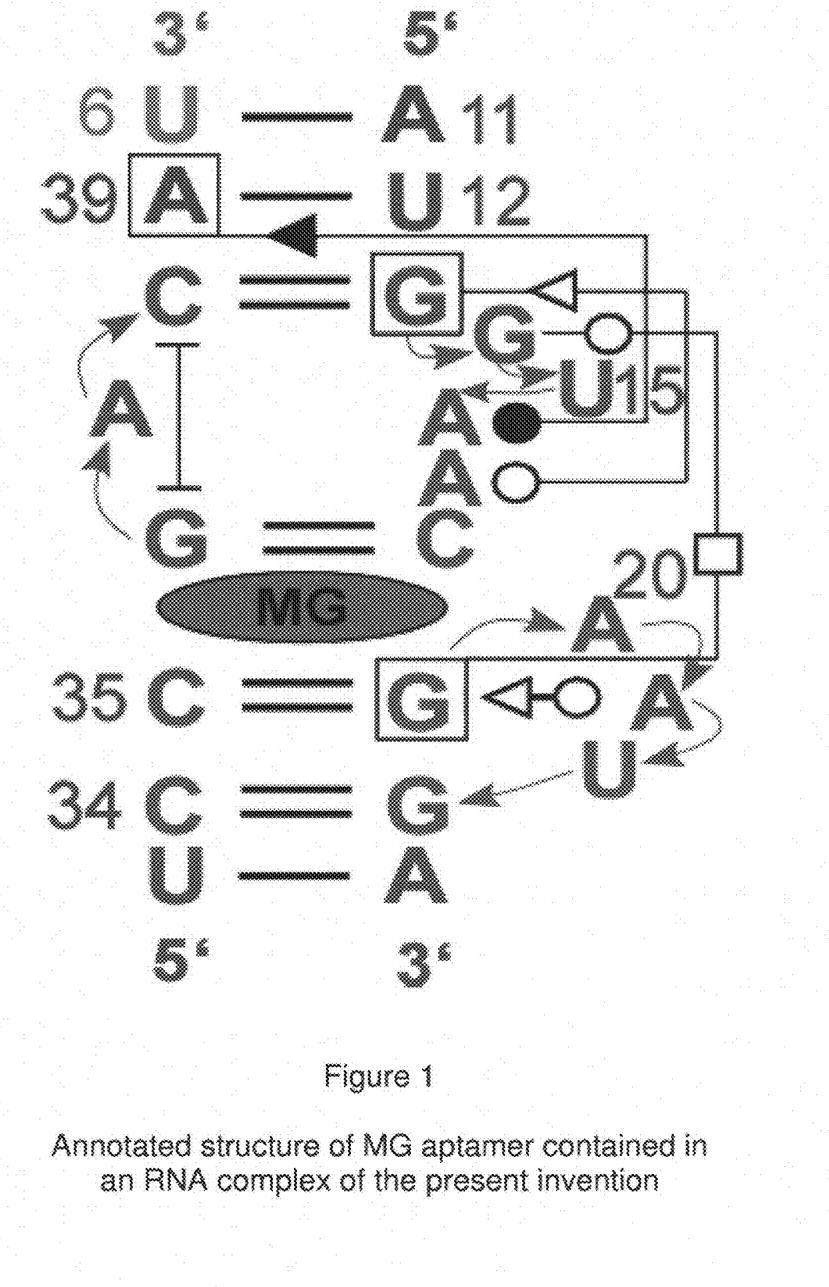
FIG. 1 shows an annotated structure of MG aptamer contained in an RNA complex, in accordance with one embodiment of the present invention.

The assembly of two RNA molecules to form the simplest possible paranemic motif, comprising two strand cross-overs and three double-helical half turns (3HT), is shown in FIG. 1A. FIG. 1B shows a paranemic motif with four crossovers and five half turns (5HT) and 1C shows another paranemic motif comprising six crossovers and seven half turns (7HT). As shown in FIG. 1, when paranemic motifs form, the component strands cross over at every possible point and form inter-molecular Watson-Crick basepairs using all the bases not involved in intra-molecular basepairs. Moreover, intra-molecular Watson-Crick basepairs are not disturbed.[26,27] All Watson-Crick basepairs in FIG. 1 are shown with vertical lines of varying lengths to depict the twist of the double helix. Dots indicate the non-Watson-Crick basepair that forms between the first U and the G of stable UUCG hairpin loops. For the interacting molecules forming the paranemic motif to be reversibly separable without denaturation, only an even number of crossovers and an odd number of half turns is permissible.[27]

Figure 8:
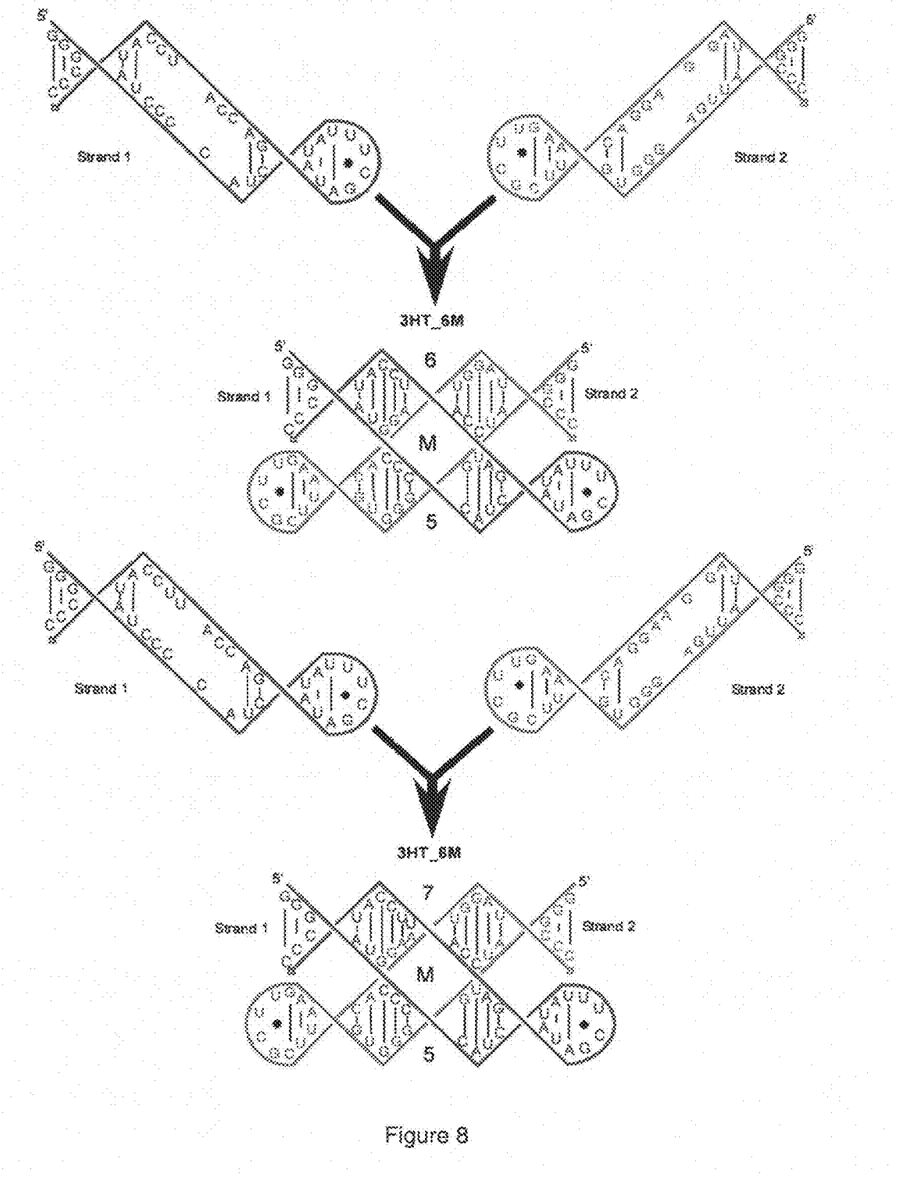
FIG. 8 shows an example of asymmetric paranemic binding, in accordance with one embodiment of the present invention.

Because it is not possible to assemble two separate strands to create a paranemic motif comprising an even number of half turns, the smallest paranemic cohesion motif comprises three helical half turns. FIG. 1 illustrates the alternating arrangement of major (M) and minor (m) grooves between cross-over points in paranemic motifs. FIG. 1D shows the correspondence between designations used for DNA and RNA paranemic assembly. Previous workers chose to use the letters "W" (for wide) and "N" (for narrow) to designate the major groove and minor grooves in DNA paranemic assembly. These designations are not appropriate for RNA, because the double helix has a narrow but deep major groove and a wide but shallow minor groove. The letter "M" designates the major groove and the letter designates "m" the minor groove, following another convention that applies to both RNA and DNA. As 3HT molecules have only two cross-over points, they can be designed so the cross-overs span either the major or minor groove. In one of the embodiments described herein, the paranemic binding may be selected so as to span the major groove as this allows for a larger number of base pairs between non-self strands. In another embodiment described in the appendix hereto, the present invention also includes paranemic assembly across the minor groove, which also may bind with as little as a minimal 3HT paranemic assembly across the minor groove. In another embodiment described in the appendix hereto, the present invention also includes paranemic assembly wherein the paranemically bound loops are non-symmetrical, such as for example by having 5-6 or 5-7 or other such varied combinations. An example of such asymmetric paranemic binding is shown in FIG. 8. Such assembly allows for further variations of the complexes of the present invention.

Molecular Dynamic simulations of paranemic crossovers in DNA have indicated that the most structurally stable arrangement for the paranemic motif entails 6 basepairs in the major groove and 5 in the minor groove.[28] Such complexes are referred to herein as "6W_5N" for DNA and "6M_5 m" for RNA.

The paranemic crossover as a cohesion motif is an attractive avenue for tecto-RNA because of the programmability of Watson-Crick base-pairing and the reversibility of binding without strand entanglement or disruption of internal helices. The present invention demonstrates the feasibility of RNA paranemic assembly, and its specificity, binding affinity, and reversibility are characterized. In accordance with the present invention, the minimal 3HT paranemic motif whether spanning the major or minor grooves, is feasible with RNA, as are other relatively small 5HT, 7HT etc. equivalents.

The present invention thus includes tectoRNA molecules that cooperatively assemble into complexes through paranemic interaction.

As used herein RNA is ribonucleic acid obtained from any source, natural or recombinant, and includes, but is not limited to RNA, mRNA, cRNA, tRNA, nRNA, rRNA and any other known or subsequently prepared or discovered RNA.

The paranemic crossover (PX) is a motif for assembling two nucleic acid molecules using Watson-Crick (WC) base-pairing without unfolding pre-formed secondary structure in the individual molecules. Once formed, the paranemic assembly motif comprises adjacent parallel double helices that cross over at every possible point over the length of the motif. The interaction is reversible as it does not require denaturation of basepairs internal to each interacting molecular unit. Paranemic assembly has been demonstrated for DNA but not for RNA, and only for motifs with four or more cross-over points and lengths of five or more helical half-turns. In the present invention includes, the design, construction, selection and use of RNA molecules that paranemically assemble with the minimum number of two cross-overs spanning the major or minor grooves to form paranemic motifs with a length of as little as three half-turns (3HT). Dissociation constants ($K_d$s) were measured for series of molecules in which the number of basepairs between the cross-over points was varied from five to eight basepairs. The paranemic 3HT complex with six basepairs (3HT_6M) was found to be the most stable with $K_d=1\cdot10^{-8}$ M. The half-time for kinetic exchange of the 3HT_6M complex was determined to be ~100 minutes, from which we calculated association and dissociation rate constants $k_a=5.11\cdot10^3$ M$^{-1}$ sec$^{-1}$ and $k_d=5.11\cdot10^{-5}$ sec$^{-1}$. RNA paranemic assembly of 3HT and 5HT complexes is blocked by single-base substitutions that disrupt individual inter-molecular Watson-Crick basepairs and is restored by compensatory substitutions that restore those basepairs. The 3HT motif appears suitable for specific, programmable, and reversible tecto-RNA self-assembly for constructing artificial RNA molecular machines.

As used herein, the term "aptamer" refers to reagents generated in a selection from a combinatorial library (typically in vitro) wherein a target molecule, generally although not exclusively a small molecule such as a metabolite or a drug, or a protein or nucleic acid, is used to select from a combinatorial pool of molecules, generally although not exclusively oligonucleotides, those that are capable of binding to the target molecule. The selected reagents can be identified as primary aptamers. The term "aptamer" includes not only the primary aptamer in its original form, but also secondary aptamers derived from (i.e., created by minimizing and/or modifying) the primary aptamer. Aptamers, therefore, must behave as ligands, binding to their target molecule. Aptamers that bind small molecules have been shown to undergo conformational changes upon interactions with their cognate ligands. A reporter fluorophore introduced into an aptamer in a region known to undergo conformational change can lead to a change in fluorescence intensity or polarization after the binding event. The use of aptamers in RNA constructs is described for instance in U.S. Pat. Nos. 6,458,559 and 6,706, 481 which are hereby incorporated herein by reference. The aptamer may also select for other types of target molecules, such as organic molecules such as pharmaceuticals, carbohydrate or other biomolecules. The role of the aptamer generally is to allow for a change in the conformation of the aptamer-containing RNA of a helical stacking domain such that its binding sites become stereochemically better disposed to binding interaction.

In the preferred embodiment, one or more fluorophore may be adapted to bind to an RNA molecule in accordance with the present invention, and which becomes active upon that RNA molecule binding paranemically to a target RNA sequence to which it conjugates.

As an example of the aptamers that may be used in accordance with the present invention, fluorescent reporters may be used. Fluorescent reporters are highly sensitive, non-perturbing, and convenient probes for biological studies. Current techniques for recognition of specific nucleic acids sequences usually require complementary hybridization to in vitro covalently labeled probes.[1] In accordance with the present invention optimal fluorescent biosensors instantly signal the presence of a specific analyte with unique selectivity and high contrast. Recent reports on several label-free fluorescent bio-indicators used aptazyme-based riboswitches as sensors for cofactors,[2] aptamer-based protein sensors,[3] and chimeric aptamer approach, in which the recognition domain that binds target coupled to the aptamer that binds fluorophore in the way that the presence of the target will affect the affinity to the fluorophore.[4,5] It is also desirable to detect macromolecular analytes (e.g. a structured RNA molecule) in a native environment without having to denature or unfold them.

The present invention also includes a technique for sensitive, label-free real-time, sequence-specific recognition of pre-folded RNA sequences by using RNA constructs with an aptameric pocket stabilized upon binding the specific analyte RNA sequence. These constructs may be referred to as "token" RNAs.

As an example of an fluorescent aptamer in accordance with the present invention, one may consider triphenylmethane dye, Malachite Green (MG), as the fluorescent reporter because in its unbound state in solution it exhibits extremely low fluorescence quantum yield from the S1 excited state due to efficient internal conversion.[6,7]

The emission of the dye increases dramatically when the non-radiative relaxation channels from S1 are shut down. While the detailed underlying mechanisms of this phenomenon are still being debated,[7-9] related studies show that "rigidifying" the dye by placing it in a highly viscous environment or in a binding cage increases its emission dramatically.[7] For instance, it was reported recently that the emission of MG increases by several orders of magnitude upon binding to an RNA aptamer obtained by in vitro selection (SELEX).[8,10] MG aptamer was previously used as a reporter for ATP recognition by linking to the ATP aptamer through a communication module.[4]

The present invention also includes a sensor based upon the compositions of matter and methods of the present invention. For instance a sensor may include a token RNA by coupling the aptamer to a three-half-turn (3HT) RNA paranemic binding motif we designed and characterized recently.[11] DNA paranemic cohesions have been investigated and utilized to assemble large objects in 2D arrays.[12-14] The 3D structure of the MG-aptamer (PDB files:1f1t and 1q8n) shows that the MG binding pocket comprises an internal loop embedded within an RNA helix.[15] The MG intercalates between a Watson-Crick basepair and a base quadruple and makes additional contacts with unpaired bases. One adenosine stacks on the phenyl group and interferes with its rotation. The annotated structure of the aptamer embedded in the sensor RNA is shown in FIG. 1.[16]

In general terms, the invention includes an RNA complex comprising two monomeric units, each comprising an RNA molecule, the monomeric units each comprising an RNA having a designed, predetermined, prescribed, selected or otherwise appropriate domain such that two monomeric units are adapted to self-assemble paranemically so as to form the RNA paranemic complex, the monomeric unit comprising an aptamer. In accordance with the present invention, other complexes are possible involving more than two monomeric units of the same or different RNA molecules.

In addition, RNA monomer(s) and/or strands that may be used in accordance with the present invention may also include any structure that is capable of forming, directly or indirectly, site-specific RNA—RNA paranemic binding interactions (i.e., such interactions that resist dissociation). These interactions may be of any type including non-Watson-Crick interaction, Watson-Crick interaction or other stereospecific non-covalent interactions. The target RNA monomer(s) and/or strands to which the analytical RNA monomer(s) is/are directed may be of any type, size or sequence.

The analytical RNA monomer(s) used to form the RNA complex of the present invention may be of any size, but typically and preferably will be a based upon at least one of the monomers being relatively small, so as to form 7HT, 5HT or 3HT paranemic assemblies when bound to target RNAs.

RNA Complex Per Se with at Least One of the Monomers Having an Aptameric Portion The present invention also includes directional and conformation-specific self-assembling RNA complexes of various sizes that include aptamers, wherein the RNA—RNA bonding or complexation is through paranemic interaction, and their application as platforms for improved aptamer-based analytic methods, biosensors and analytic devices.

The invention further includes an RNA complex as described otherwise herein comprising a target RNA molecule (typically bearing a sequence such that it is in the position of an analyte RNA or RNA sequence whose presence is to be determined) and a monomeric unit comprising an RNA having a binding domain, such that the target RNA molecule and the RNA monomeric unit have a binding domain adapted to self-assemble paranemically so as to form an RNA complex, the RNA monomeric unit comprising an aptameric portion, typically held within or near the binding domain by some binding or other interaction, such as described and exemplified herein.

The aptameric portion typically is adapted to bind a fluorophore whose fluorescence activity is altered by the binding of the target RNA molecule and the RNA monomeric unit, such that its level of fluorescence increases or decreases upon paranemic interaction. The fluorophore may be any compound or substance capable of binding or complexing with the RNA monomeric unit, and whose fluorescence activity is altered by the binding of the target RNA molecule and the RNA monomeric unit. Examples may include organic dyes such as Malachite Green. It will be appreciated that the invention includes variations wherein the aptameric portion may participate in the self-assembling paranemic binding.

It is preferred for ease of manufacture, use and handling that the monomeric unit comprising an RNA molecule has a helical domain of less than 7 half turns, such as 5 half turns and most preferably less than 5 half turns, such as 3 half turns. Typically, the RNA monomeric unit will be smaller than the target RNA to which it is directed and complexed.

The monomeric unit comprising an RNA molecule may be produced in vitro, but may also be provided in vivo such as through insertion by way of a virus. The complexation likewise may be made to occur in vitro or in vivo, and may be made to occur in tissue or in living organisms.

It is also preferred that the monomeric unit be in the form of a loop closed by non-Watson-Crick interactions, although a number of other configurations may be possible that provide the binding capability for fluorophore with the requisite fluorescence alteration characteristics. The RNA monomeric unit typically and preferably will bind the fluorophore through interaction with basepairs within the loop, as shown by example in the drawings.

The present invention also includes an RNA complex as described wherein the aptameric portion is adapted to bind a fluorophore, and comprises a fluorophore.

In the present invention, the role of the aptamer is to provide a change in state that can be detected so as to be able to determine the interaction between the RNA monomer and the target RNA.

In the preferred embodiment, the aptamer(s) may be one or more fluorophores adapted to bind to an RNA molecule in accordance with the present invention, and which becomes active upon that RNA molecule binding paranemically to a target RNA strand to which it conjugates. Although not limited by the theory of the invention, the paranemic binding in some embodiments causes an alteration in the three-dimensional structure of the aptameric portion, such as a strengthening or stiffening, which in turn causes a change in the fluorescent activity of the bound fluorophore.

In still another optional embodiment of the present invention, the RNA monomeric unit as described herein may additionally comprise a portion, typically held within or near the aptameric portion, and adapted to provide a quantum dot structure such that the fluorescent activity of the bound fluorophore is enhanced. Quantum dot structures and methods for incorporating them into biomolecules are known in the art. Examples of such quantum dot structures include water-soluble luminescent quantum dots, a biomolecular conjugate thereof and a composition comprising such quantum dots or conjugates, and methods of obtaining a luminescent quantum dot, a method of making a biomolecular conjugate thereof, and methods of using a biomolecular conjugate for ultrasensitive nonisotopic detection in vitro and in vivo are described in U.S. Pat. No. 7,192,785, incorporated herein by reference.

The monomers may be designed or selected so as to self-assemble into trimers, tetramers, pentamers, hexamers, heptamers or octamers, or even more complex closed shapes with the target RNA as described herein. It will be understood that, although described with respect to the interaction between an RNA monomer and a target RNA, the invention also includes more complex interactions such as interactions between one or more RNA monomer(s) and one or more target RNA(s), which may give rise to more complex interactions allowing for greater specificity in the target RNA(s) detected or distinguished from one another within the same sample.

Accordingly, it will be appreciated that, in other variations of the present invention, more than one RNA complex may be formed from two RNA monomers specific for different regions of a single target RNA, one RNA monomer specific for the same region of different target RNAs, etc. Accordingly, the present invention includes any of the wide variety of one or more combinations of one or more RNA monomers complexing with one or more compounds, compositions or sequences containing respective one or more target RNAs. For instance, one single target RNA may be assayed through the use of the present invention for more than one different sequences, either qualitatively or quantitatively. Alternatively, two different target RNAs in a sample may be analyzed, either qualitatively or quantitatively, for their presence by determining the presence of different representative RNA sequences.

Method of Forming an RNA Complex with the RNA Monomer Having an Aptameric Portion Bearing a Fluorophore The present invention also included biosensors and analytical methods based on cooperative token RNA complexes, which may be based upon the effects of RNA self-assembly on the affinity and cooperativity of RNA analyte binding.

The present invention includes a method of making a self-assembled RNA complex comprising the steps: (a) placing in solution a target RNA; (b) a monomeric unit comprising an RNA having a helical domain adapted to self-assemble paranemically with the target RNA, and the binding domain comprising an aptameric portion bound to a fluorophore; and (c) allowing the monomeric unit comprising an RNA having a binding domain to bind to the target RNA paranemically so as to form the RNA complex whereby the fluorescence of the fluorophore increases above that when bound to the uncomplexed monomeric unit comprising an RNA.

Method of Determining Presence of an RNA by Formation of an RNA Complex with a Monomer Having an Aptamer Bound to a Fluorophore A method of determining the presence and/or amount of an analyte through the formation a self-assembled RNA complex, the method comprising the steps: (a) placing in solution an analyte such as one or more target RNAs or target composition comprising one or more target RNAs; (b) a monomeric unit comprising an RNA having a binding domain adapted to self-assemble paranemically with the target RNA, and the binding domain comprising an aptameric portion bound to a fluorophore; and (c) allowing the monomeric unit comprising an RNA having a binding domain to bind to the target RNA paranemically so as to form the RNA complex whereby the fluorescence of the fluorophore changes in comparison to that when bound to the uncomplexed monomeric unit comprising an RNA; (d) detecting the change in fluorescence of the fluorophore between the uncomplexed and complexed state of the target RNA and the monomeric unit comprising an RNA.

As can be appreciated from the present disclosure, the present invention may be applied with beneficial effect to any of a wide variety of biological molecules comprising or bound to RNA moieties or constructs. Likewise, a wide variety of known techniques and methods, such as electrophoresis, may be applied to complexes of the present invention for further analysis.

In many embodiments, the fluorophores may be detected using any of several techniques, such as enhanced chemiluminescence (ECL), fluorescence counters, etc. The change in fluorescence of the fluorophore (whether increasing or decreasing) may be determined by any method, such as by a method selected from the group consisting of steady-state and time-resolved optical techniques including steady-state emission, time resolved photoluminescence and fluorescence upconversion spectroscopies.

Sensor for Determining Presence of an RNA Complex with at Least One of the Monomers Having an Aptamer Bearing a Fluorophore The present invention also includes a sensor adapted to bind an analyte RNA, the sensor comprising (a) a vessel containing: (i) a target RNA; (ii) a monomeric unit comprising an RNA having a binding domain adapted to self-assemble paranemically with the target RNA so as to form an RNA complex, and the binding domain comprising an aptameric portion bound to a fluorophore such that the fluorescence of the fluorophore changes when the monomeric unit comprising an RNA binds to the target RNA; and (b) a detector to detect the change (increase, from an original signal or no signal, or decrease) in fluorescence of the fluorophore between the uncomplexed and complexed state of the target RNA and the monomeric unit comprising an RNA.

The change in fluorescence may be determined by any functionally appropriate device or detector as will be appreciated from the specific application of the present invention, such as a commercially available fluorescence detector.

RNA Monomer Per Se Comprising Aptameric Portion Bound to a Fluorophore

The present invention also includes an RNA monomeric unit, the monomeric unit comprising an RNA having a binding domain are adapted to self-assemble paranemically so as to form an RNA complex with another RNA, the binding domain of the RNA monomeric unit comprising an aptameric portion bound to a fluorophore.

The invention further includes an RNA complex as described otherwise herein comprising at least two monomeric units of RNA at least one of which has a binding domain comprising a fluorescent moiety.

These fluorescent variations of the RNA complexes of the present invention may be used as analytical markers, such as in analytical schemes described herein. The present invention may be applied in any analytical or diagnostic setting wherein the discrete detection of one or more RNA sequences, typically pre-determined or identified, is desired.

The present invention therefore is a variation and improvement upon the invention described in co-pending U.S. patent application Ser. No. 11/196,003 in that it provides many of the same benefits while being based upon paranemic interactions rather than the receptor-loop interactions as described therein. Accordingly, the same uses of the complexes of the present invention may be binding and made more readily, and used for analytic or diagnostic purposes, using corresponding experimental schemes and arrangements to create sensors and devices as will be appreciated from this disclosure.

Asymmetric Paranemic Binding

Another variation of the present invention is the use of pairs of asymmetric paranemically bound pairs of RNA loops.

Figure 9:
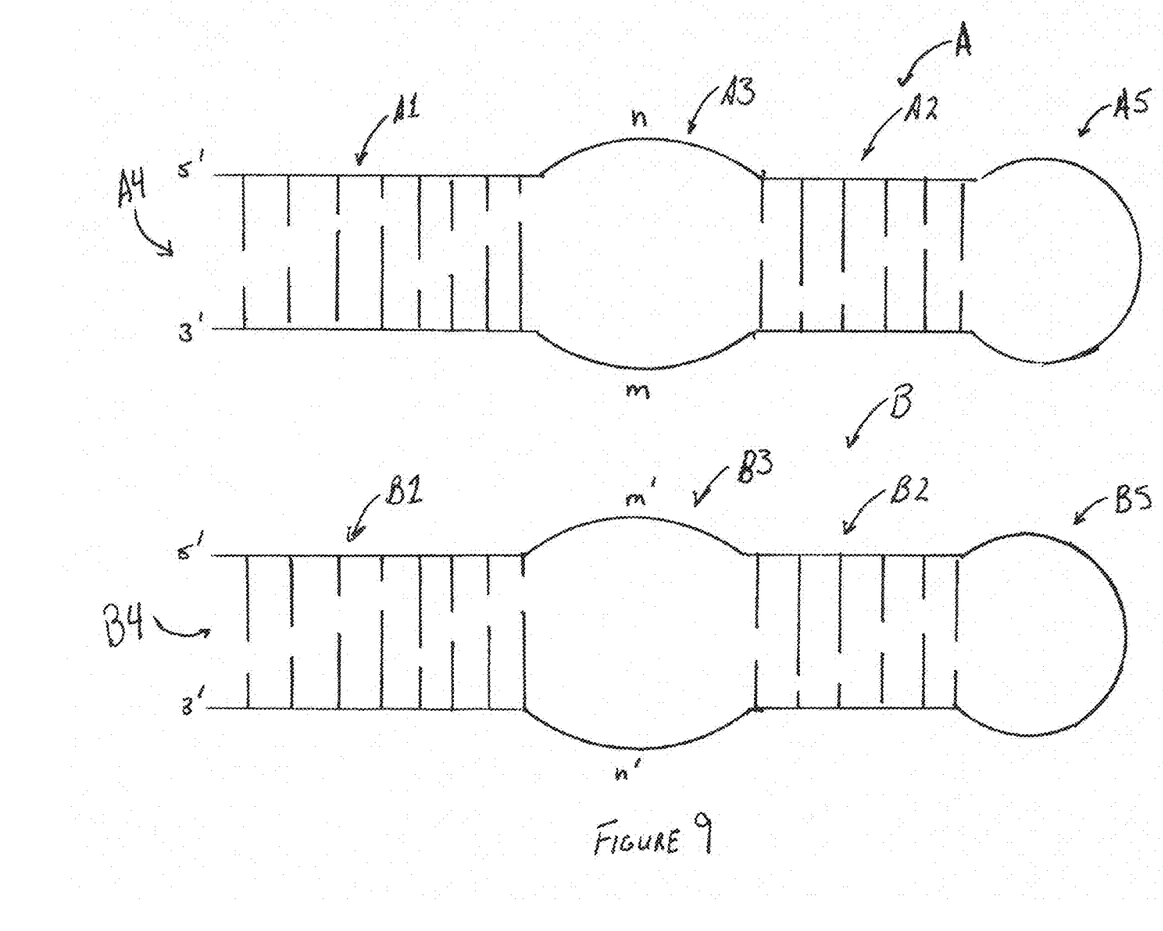
FIG. 9 shows a general example of asymmetric paranemic binding, in accordance with one embodiment of the present invention.

This aspect of the present invention may be understood generally by reference to FIG. 9. This Figure shows a general representation of two RNA loop structures A and B that have helical regions (A1 and A2, and B1 and B2, respectively) on either side of a central strand (A3 and B3, respectively) that does not bind to an opposed strand within the loop in a Watson-Crick manner. Each RNA loop structure A and B also have respective 5' and 3' ends (A4 and B4, respectively), and terminal loop ends (A5 and B5, respectively). It will be understood that the invention is not limited to the length of these regions or their individual nucleotide sequences, but rather is intended to encompass all variations of the described generic structure.

As shown in FIG. 9, in structures A and B, the prior art teaches such structures to be paranemically bound wherein n is equal to m and n' is equal to m'; n being complimentary to n' in the Watson-Crick sense and m being complimentary to m' in the Watson-Crick sense. By contrast, in the structures and complexes of the present invention, the complexes are asymmetric in that n is not equal to m and n' is not equal to m' while n is equal to n' and m is equal to m'.

The present invention thus includes the formation of stable paranemic motifs using stable non-Watson-Crick paired motifs that are more stable than the corresponding Watson-Crick helices. This variation may be understood as providing complexes and their constituent monomers, wherein the complexes have an opposed asymmetric non-Watson-Crick bound portions, and the stable non-Watson-Crick paired motifs thereof. The monomers and complexes of the present invention may be understood by reference to the complexes and the preferred embodiments of the present invention as described herein and shown in the drawings, by incorporating the described asymmetry. In accordance with the present invention as otherwise described herein, the binding may be along the major or minor groove, although it is preferred and more likely that binding occur along the major groove. However, whether on the major or minor groove, this does not affect the asymmetric paranemic binding itself. The paranemic binding does occur, and it does not matter if it is on the major or minor groove, which may depend on the motif which side the crossovers occur on.

The monomers and complexes of the present invention may includes the aptamers and/or fluorophores in accordance with the preferred embodiments of the present invention as described herein and shown in the drawings, by incorporating same as is done in accordance with other embodiments of the present invention.

The complexes of the present invention may be used in various ways where one may benefit from asymmetric paranemic binding. Examples include binding and attendant inhibition of vivoids (plant pathogens), and sensing for microbial ecology with relatively high throughput. Other applications are possible. For instance, given that many micro-RNAs bind their targets to form asymmetric internal motifs, one could use paranemic binding to simultaneously trap a micro-RNA bound to its target. This may be an important application as finding miRNA targets remains a challenge.

The present invention thus includes an RNA complex comprising a target RNA molecule and a monomeric unit comprising an RNA having a binding domain, such that the target RNA molecule and the monomeric unit comprising an RNA having a binding domain are adapted to self-assemble paranemically so as to form said RNA complex, the monomeric unit comprising an aptameric portion, and having an opposed asymmetric non-Watson-Crick bound portions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Samples contained fixed amounts of radiolabeled 3652* (0.5 nM) and cold (0.2 µM) cognate partners.

DETAILED DESCRIPTION OF THE PREFERRED EMBODIMENTS

In accordance with the foregoing summary of the invention, the following presents a detailed description of the preferred embodiments, which are considered to be the best mode thereof.

Figure 2:
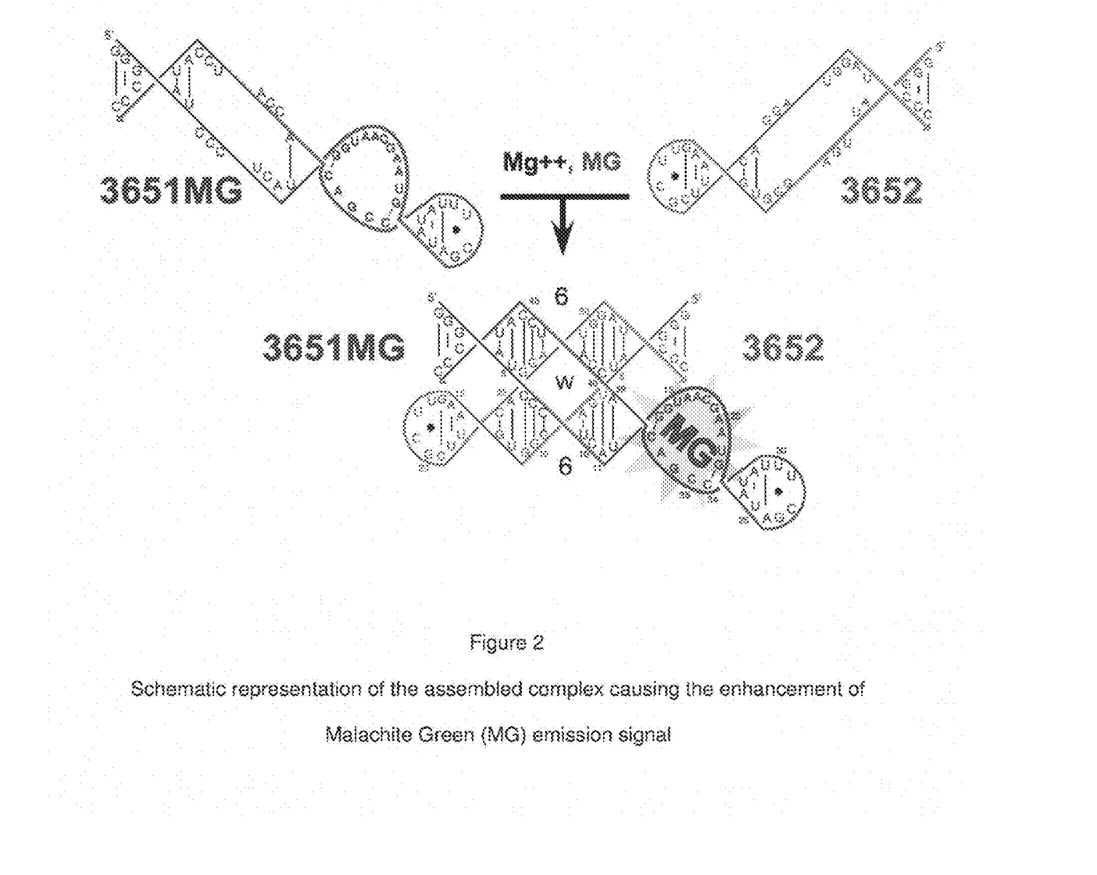
FIG. 2 shows a schematic representation of the assembled complex causing the enhancement of Malachite Green (MG) emission signal, in accordance with one embodiment of the present invention.

In the preferred embodiment of the present invention, an aptamer internal loop positioned close to the paranemic binding site so the helix flanking the aptamer and stabilizing it can only form when the sensor RNA binds to a target (analyte) RNA containing the complementary sequence. When the sensor binds the complementary target strand, the aptamer's binding site is stabilized, and therefore it can bind MG. 3D modeling was employed to examine alternative positions and orientations of the MG aptamer relative to the paranemic binding motif. The orientation was chosen so that flanking Watson-Crick basepairs of the aptamer that form stabilizing base triples with "unpaired" aptamer adenosines are adjacent to the paranemic site. Different constructs were tested to find the optimal number of basepairs separating the aptamers from the paranemic site and the final design with the scheme of assemble is shown in FIG. 2, which is a schematic representation of the assembled complex causing the enhancement of Malachite Green (MG) emission signal.

The molecules were named according to the number of half-turns (3) and the number of basepairs separating the strand cross-over points across the major (wide) groove (6). "MG" added to the name of a molecule indicates the presence of the MG aptamer sequence in the RNA molecule.

All RNA molecules were run-off transcribed from DNA templates having T7 RNA polymerase promoter regions and purified on denaturing gels. Assembly experiments were carried out using native gels as previously described[17] to assay assembly in the presence and absence of MG. The 3651/3652 dimer was used as a gel mobility control. Radio-labeled 3652 was mixed with its cognate partners—3651, and 3651 MG with and without MG in the solution. The gel presented in the Supporting Information, FIG. 1 shows that 3651 MG binds to 3652 and the presence of MG is not essential for this process.

Having demonstrated from the gel assembly experiments that 3652 and 3651MG assemble (FIG. 1, S.I.), the MG emission upon excitation at 425 nm was measure (FIG. 2) using a Jobin Yvon Fluorolog 3-11 spectrofluorimeter, as detailed in the Supporting Information below.

When MG was added to the aptamer-containing token RNA, 3651 MG, in the absence of the RNA target 3652, the MG emission remained very low, similar to that of free MG. However, when MG was added to 3651MG in the presence of 3652, the fluorescence of MG increased dramatically. Although not limited by theory of the invention this appears to indicate that paranemic assembly of the sensor with the target is required to stabilize the aptameric pocket possibly by allowing stabilizing non-Watson-Crick basepairs to form. These basepairs include A39-A16, G13-A17, G14-G19, G19-A21 (FIG. 1).

Figure 4:
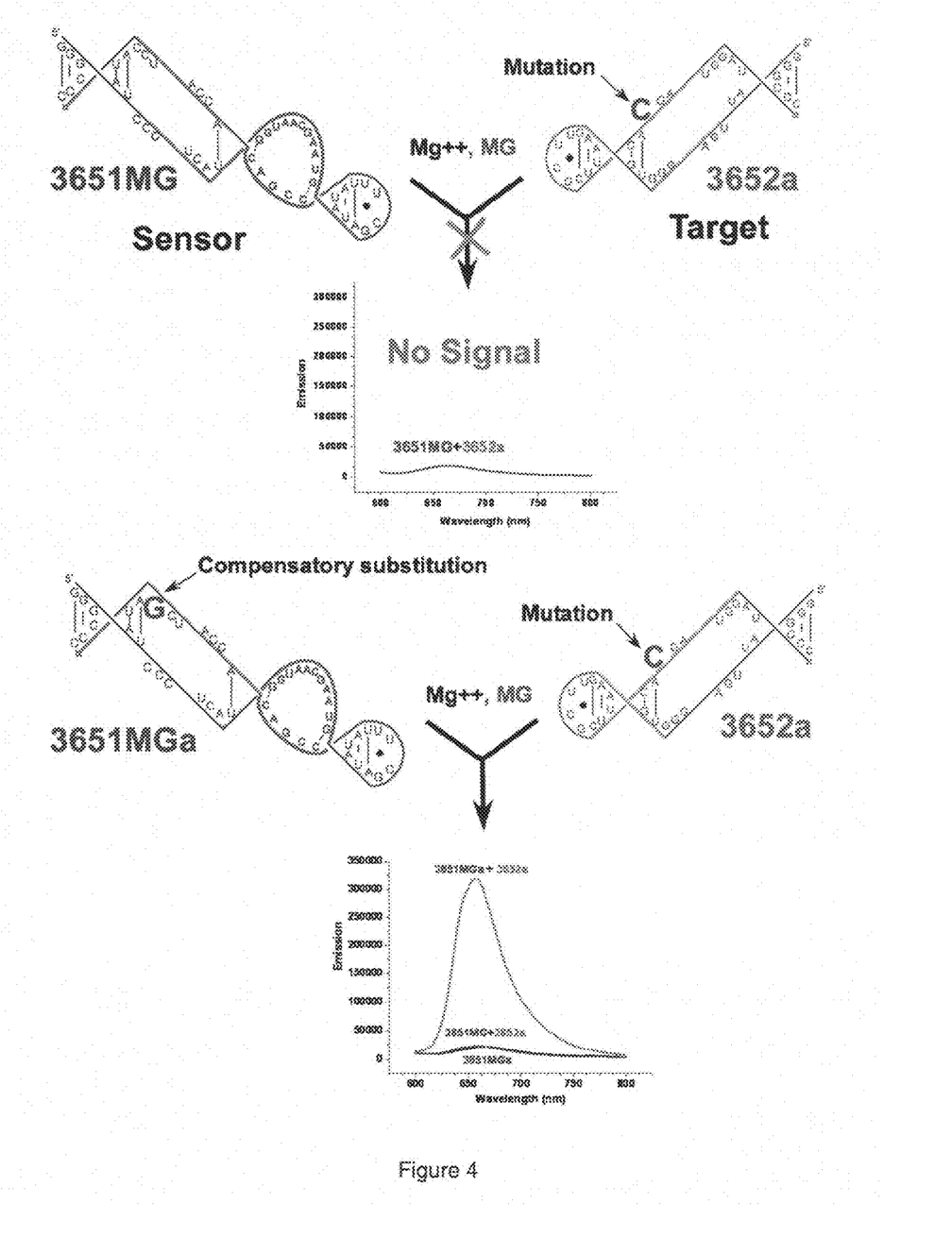
FIG. 4 shows a schematic representation of the sequence specificity of detection and related spectra of RNA complexes, in accordance with one embodiment of the present invention.

To determine the specificity of the sensor for its target, point mutations were introduced in the target molecule (see FIG. 4). The altered molecules are designated 3652a and 3652c. Molecules 3651 MGa, and 3651 MGc were prepared molecules are identical to 3651MG except for the base changes illustrated in FIG. 2 (S.I.). FIG. 4 shows a schematic representation of the sequence specificity of detection and related spectra. In the upper scheme, a single point mutation (G→C) prevents the assembly and cause no signal of emission. In the bottom scheme, compensatory substitution (C→G) supports dimerization and turns on Malachite Green (MG) emission signal.

Differently colored letters demonstrate structural mutations made within 3651 MG and compensations within 3652 molecules. These changes occur only in the wide crossover grooves, and should not affect the free energy of folding of individual strands as was shown in previous work.

Figure 3:
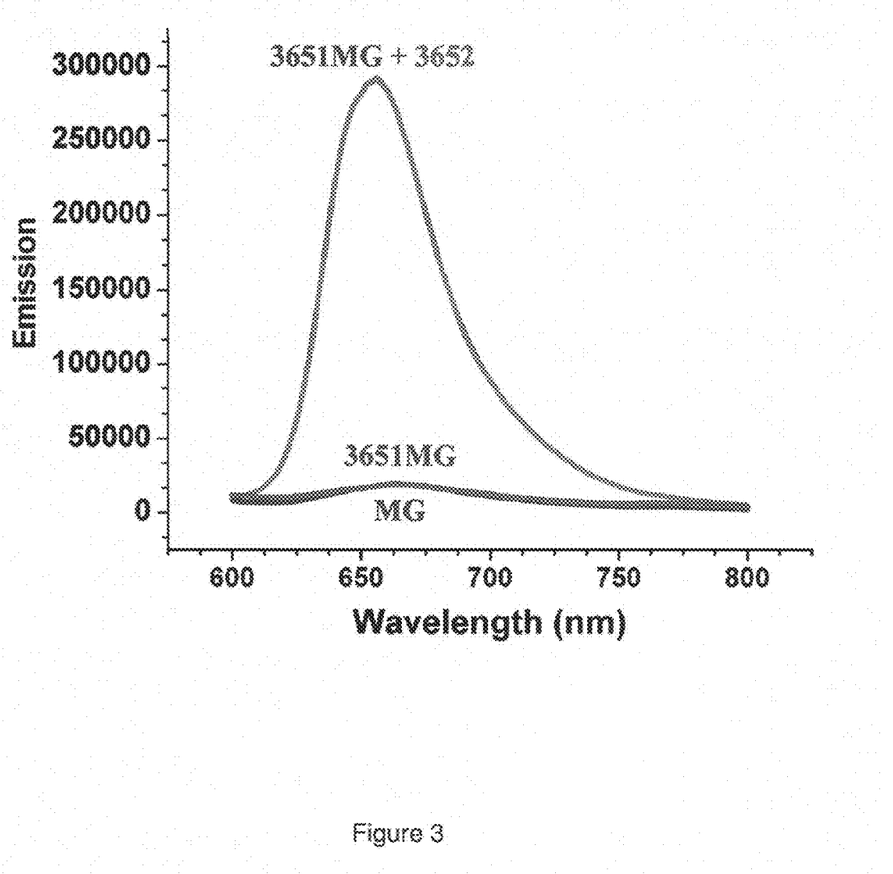
FIG. 3 shows a graph of emission vs. wavelength demonstrating how an MG aptamer enhances the fluorescence of MG upon the assembly, in accordance with one embodiment of the present invention.

In the presence of 3651 MGa (FIG. 3) and 3651 MGc (FIG. 2, S.I.) MG does not emit. Also fluorescence of MG was measured in the presence of 3651 MG/3652a and 3651 MG/3652a. The results show that when the complementary strand has only a single base mismatch in a crossover groove there is no signal of MG emission. While sequences with compensations of the mutations (3651 MGa/3652a, and 3651 MGc/3652c) enhance the signal of MG tremendously. It indicates that a single WC mismatch in a crossover groove severely compromises assembly. These data confirm the results from previous work (Paran), where equilibrium favors the monomer when the complementary strand has only a single base mismatch in a crossover groove.

Accordingly, the present invention demonstrates that incorporating MG aptamer into tectoRNA molecules has a potential to systematically create new biosensors for prefolded nucleotide sequences recognition and analysis. The present invention also provides very high specificity of this system by virtue of the impossibility to assemble in cases with as little as a single WC mismatch in a crossover groove, and as the result the complete absence of MG fluorescent signal in this example embodiment.

Figure 5:
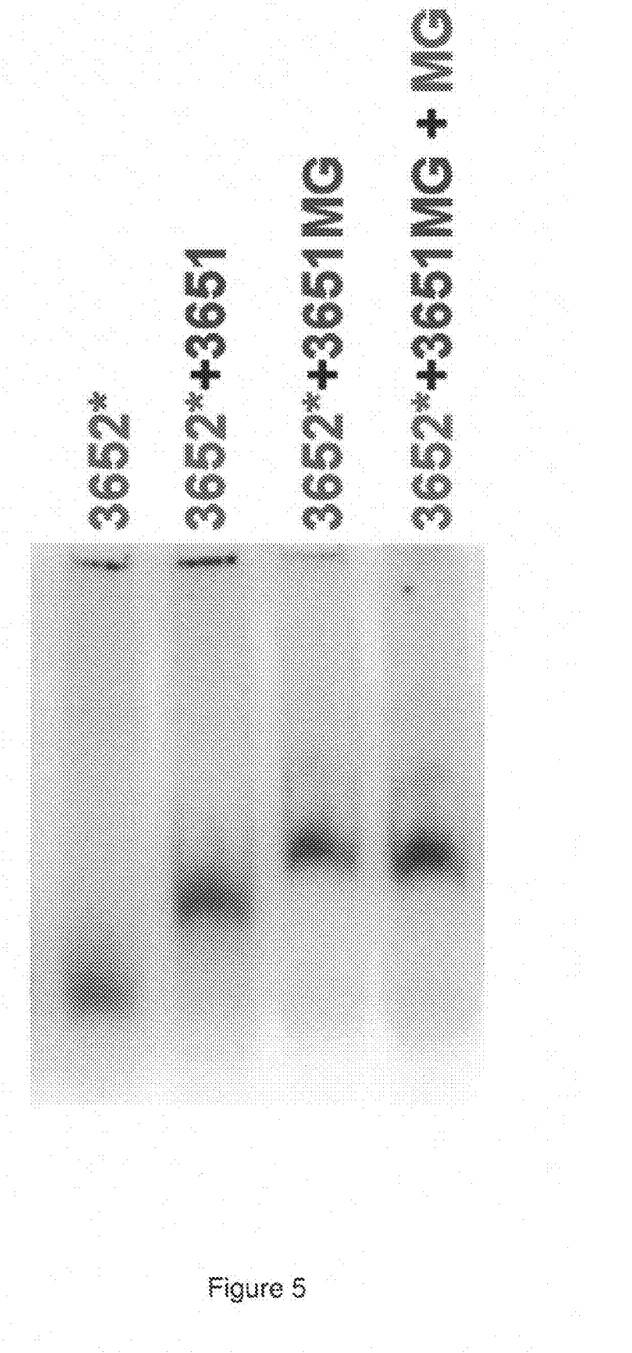
FIG. 5 shows gel electrophoresis with non-denaturing polyacrylamide gel showing the assembly of an MG aptamer containing molecule 3651 MG with 3652 with and without MG presence, in accordance with one embodiment of the present invention.

FIG. 5 shows gel electrophoresis with non-denaturing polyacrylamide gel showing the assembly of an MG aptamer containing molecule 3651MG with 3652 with and without MG presence. Samples contained fixed amounts of radiolabeled 3652*(0.5 nM) and cold (0.2 µM) cognate partners.

Figure 6:
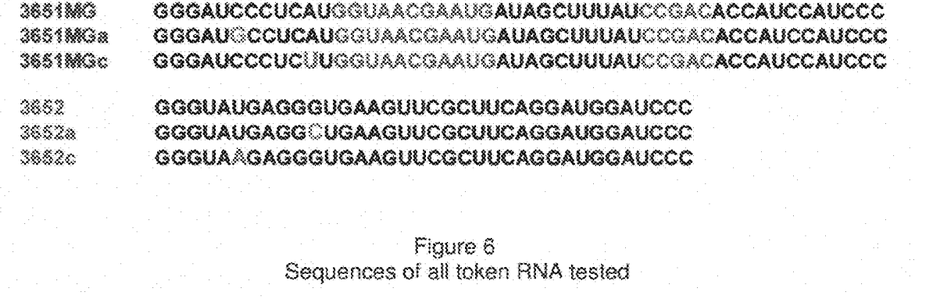
FIG. 6 is the RNA sequence listing of SEQ. ID 1, SEQ. ID 2, SEQ. ID 3, SEQ. ID 4, SEQ. ID 5, and SEQ. ID 6, the token RNA tested, in accordance with one embodiment of the present invention

FIG. 6 shows the RNA sequences of all token RNA tested, in accordance with this embodiment of the present invention.

Figure 7:
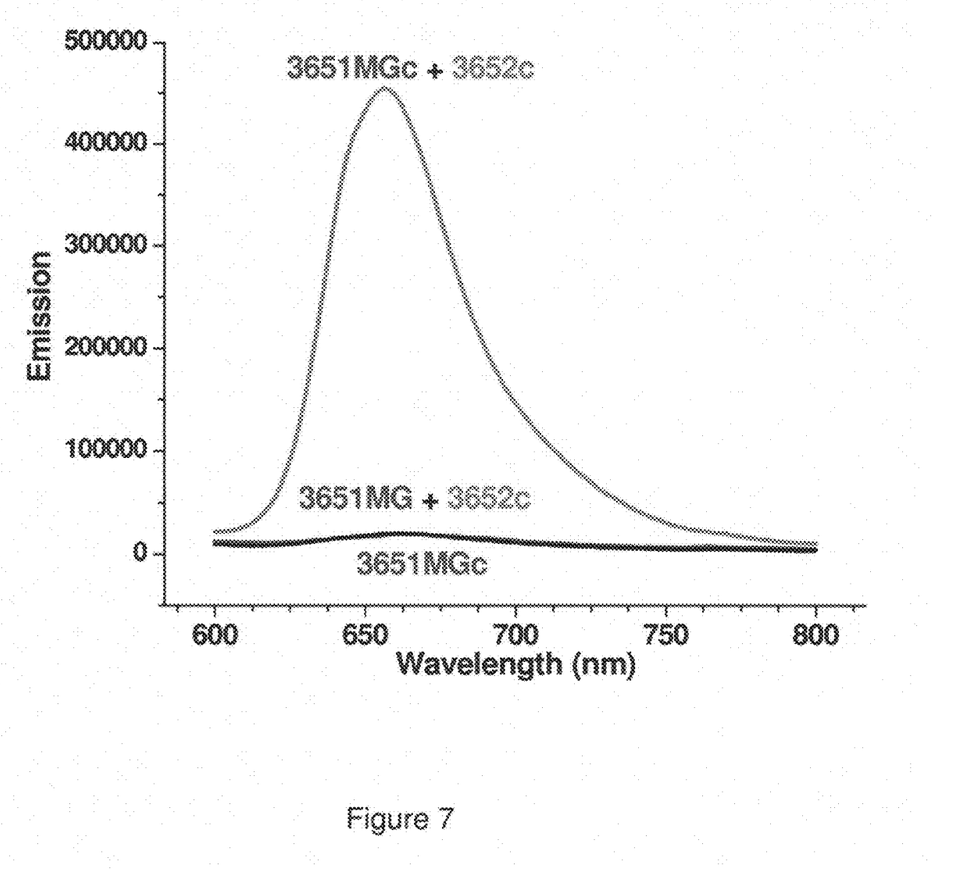
FIG. 7 shows a graph of emission vs. wavelength demonstrating sequence specificity of detection of target RNA 3652c having a point mutation with 3651 MG and 3651 MGc—having a compensational mutation.

FIG. 7 shows a graph of emission vs. wavelength demonstrating sequence specificity of detection of target RNA 3652c having a point mutation with 3651 MG and 3651 MGc—having a compensational mutation. Emission spectra of MG with 3651 MGa (black), MG with 3651 MG and mutated 3652c (blue), and MG with the compensated complex 3651 MGc/3652c (red).

The experimental details for the emission studies were as follows: Starting wavelength—600 nm; Ending wavelength—800 nm; Increment 2; Excitation—425 nm; Integration time 1s; Detector voltage—950V; Signal—cps; Emission Acquisition: Excitation—4.0 nm; Emission—4.0 nm.

While certain preferred embodiments of the present invention have been described and specifically exemplified above, it is not intended that the invention be limited to such embodiments. Various modifications may be made to the invention without departing from the scope and spirit thereof as set forth in the following claims.

REFERENCES

1. Long, R. M.; Elliott, D. J.; Stutz, F.; Rosbash, M.; Singer, R. H., Spatial consequences of defective processing of specific yeast mRNAs revealed by fluorescent in situ hybridization. *RNA* 1995, 1, (10), 1071-1078.
2. Ogawa, A.; Maeda, M., Aptazyme-based riboswitches as label-free and detector-free sensors for cofactors. *Bioorg Med Chem Lett* 2007, 17, (11), 3156-60.
3. Jiang, Y.; Fang, X.; Bai, C., Signaling aptamer/protein binding by a molecular light switch complex. *Anal Chem* 2004, 76, (17), 5230-5.
4. Stojanovic, M. N.; Kolpashchikov, D. M., Modular aptameric sensors. *J Am Chem Soc* 2004, 126, (30), 9266-70.
5. Wu, L.; Curran, J. F., An allosteric synthetic DNA. *Nucleic Acids Res* 1999, 27, (6), 1512-6.
6. Baptista, S. B.; Indig, G. L., Effect of BSA binding on photophysical and photochemical properties of triarylmethane dyes. *J. Phys. Chem.* 1998, 102, 4678-4688.

7. Duxbury, D. F., The Photochemistry and Photophysics of Triphenilmethane Dyes in Solid and Liquid Media. *Chem. Rev.* 1993, 93, 381-433.
8. Babendure, J. R.; Adams, S. R.; Tsien, R. Y., Aptamers switch on fluorescence of triphenylmethane dyes. *J Am Chem Soc* 2003, 125, (48), 14716-7.
9. Nguyen, D. H.; DeFina, S. C.; Fink, W. H.; Dieckmann, T., Binding to an RNA aptamer changes the charge distribution and conformation of malachite green. *J Am Chem Soc* 2002, 124, (50), 15081-4.
10. Grate, D.; Wilson, C., Laser-mediated, site-specific inactivation of RNA transcripts. *Proc Natl Acad Sci USA* 1999, 96, (11), 6131-6.
11. Afonin, K. A.; Cieply, D. J.; Leontis, N. B., Specific RNA Self-assembly with Minimal Paranemic Mofifs. *J Am Chem Soc* in press. Copy of draft attached as an Appendix
12. Zhang, X.; Yan, H.; Shen, Z.; Seeman, N. C., Paranemic cohesion of topologically-closed DNA molecules. *J Am Chem Soc* 2002, 124, (44), 12940-1.
13. Constantinou, P. E.; Wang, T.; Kopatsch, J.; Israel, L. B.; Zhang, X.; Ding, B.; Sherman, W. B.; Wang, X.; Zheng, J.; Sha, R.; Seeman, N. C., Double cohesion in structural DNA nanotechnology. *Org Biomol Chem* 2006, 4, (18), 3414-9.
14. Shen, Z.; Yan, H.; Wang, T.; Seeman, N. C., Paranemic crossover DNA: a generalized Holliday structure with applications in nanotechnology. *J Am Chem Soc* 2004, 126, (6), 1666-74.
15. Flinders, J.; DeFina, S. C.; Brackett, D. M.; Baugh, C.; Wilson, C.; Dieckmann, T., Recognition of planar and non-planar ligands in the malachite green-RNA aptamer complex. *Chembiochem* 2004, 5, (1), 62-72.
16. Baugh, C.; Grate, D.; Wilson, C., 2.8 A crystal structure of the malachite green aptamer. *J Mol Biol* 2000, 301, (1), 117-28.
17. Afonin, K. A.; Leontis, N. B., Generating new specific RNA interaction interfaces using C-loops. *J Am Chem Soc* 2006, 128, (50), 16131-7.
Ball, P. (2002). "Natural Strategies for the Molecular Engineer." *Nanotechnology* 13: R15-R28.
Cate, J. H., A. R. Gooding, E. Podell, K. Zhou, B. L. Golden, C. E. Kundrot, T. R. Cech and J. A. Doudna (1996). "Crystal structure of a group I ribozyme domain: principles of RNA packing." *Science* 273(5282): 1678-85. [http://www.ncbi.nlm.nih.gov/entrez/query.fcgi?cmd=Retrieve&db= PubMed&dopt= Citation&list_uids=8781224]
Cate, J. H., A. R. Gooding, E. Podell, K. Zhou, B. L. Golden, A. A. Szewczak, C. E. Kundrot, T. R. Cech and J. A. Doudna (1996). "RNA tertiary structure mediation by adenosine platforms." *Science* 273(5282): 1696-9. [http://www.ncbi.nlm.nih.gov/entrez/query.fcgi?cmd=Retrieve&db= PubMed&dopt= Citation&list_uids=8781229]
Costa, M. and F. Michel (1997). "Rules for RNA recognition of GNRA tetraloops deduced by in vitro selection: comparison with in vivo evolution." *Embo J* 16(11): 3289-302. [http://www.ncbi.nlm.nih.gov/entrez/query.fcgi?cmd=Retrieve&db= PubMed&dopt= Citation&list_uids=9214644]
Emilsson, G. M. and R. R. Breaker (2002). "Deoxyribozymes: new activities and new applications." *Cell Mol Life Sci* 59(4): 596-607. [http://www.ncbi.nlm.nih.gov/entrez/query.fcgi?cmd=Retrieve&db=PubMed&dopt= Citation&list_uids=12022469]
Ennifar, E., P. Walter, B. Ehresmann, C. Ehresmann and P. Dumas (2001). "Crystal structures of coaxially stacked kissing complexes of the HIV-1 RNA dimerization initiation site." *Nat Struct Biol* 8(12): 1064-8. [http://www.ncbi.nlm.nih.gov/entrez/query.fcgi?cmd=Retrieve&db= PubMed&dopt= Citation&list_uids=11702070]
Fritz, J., M. K. Bailer, H. P. Lang, H. Rothuizen, P. Vettiger, E. Meyer, H. Guntherodt, C. Gerber and J. K. Gimzewski (2000). "Translating biomolecular recognition into nanomechanics." *Science* 288(5464): 316-8. [http://www.ncbi.nlm.nih.gov/entrez/query.fcgi?cmd=Retrieve&db= PubMed&dopt= Citation&list_uids=10764640]
Fu, T. J. and N. C. Seeman (1993). "DNA double-crossover molecules." *Biochemistry* 32(13): 3211-20. [http://www.ncbi.nlm.nih.gov/entrez/query.fcgi?cmd=Retrieve&db=PubMed&dopt= Citation&list_uids=8461289]
Goodsell, D. S. and A. J. Olson (2000). "Structural symmetry and protein function." *Annu Rev Biophys Biomol Struct* 29: 105-53. [http://www.ncbi.nlm.nih.gov/entrez/query.fcgi?cmd=Retrieve&db=PubMed&dopt= Citation&list_uids=10940245]
Hermann, T. (2000). "Strategies for the Design of Drugs Targeting RNA and RNA-Protein Complexes." *Angew Chem Int Ed Engl* 39(11): 1890-1904. [http://www.ncbi.nlm.nih.gov/entrez/query.fcgi?cmd=Retrieve&db=PubMed&dopt= Citation&list_uids=10940979]
Hofacker, I. L. (2003). "Vienna RNA secondary structure server." *Nucleic Acids Res* 31(13): 3429-31. [http://www.ncbi.nlm.nih.gov/entrez/query.fcgi?cmd=Retrieve&db= PubMed&dopt= Citation&list_uids=12824340]
Hohng, S., T. J. Wilson, E. Tan, R. M. Clegg, D. M. Lilley and T. Ha (2004). "Conformational flexibility of four-way junctions in RNA." *J Mol Biol* 336(1): 69-79. [http://www.ncbi.nlm.nih.gov/entrez/query.fcgi?cmd=Retrieve&db= PubMed&dopt= Citation&list_uids=14741204]
Jaeger, L. and N. B. Leontis (2000). "Tecto-RNA: One-Dimensional Self-Assembly through Tertiary Interactions This work was carried out in Strasbourg with the support of grants to N.B.L. from the NIH (1R15 GM55898) and the NIH Fogarty Institute (1-F06-TW02251-01) and the support of the CNRS to L.J. The authors wish to thank Eric Westhof for his support and encouragement of this work." *Angew Chem Int Ed Engl* 39(14): 2521-2524. [http://www.ncbi.nlm.nih.gov/entrez/query.fcgi?cmd=Retrieve&db= PubMed&dopt= Citation&list_uids=10941124]
Jaeger, L., E. Westhof and N. B. Leontis (2001). "TectoRNA: modular assembly units for the construction of RNA nanoobjects." *Nucleic Acids Res* 29(2): 455-63. [http://www.ncbi.nlm.nih.gov/entrez/query.fcgi?cmd=Retrieve&db= PubMed&dopt= Citation&list_uids=11139616]
Kertsburg, A. and G. A. Soukup (2002). "A versatile communication module for controlling RNA folding and catalysis." *Nucleic Acids Res* 30(21): 4599-606. [http://www.ncbi.nlm.nih.gov/entrez/query.fcgi?cmd=Retrieve&db= PubMed&dopt= Citation&list_uids=12409449]
Klostermeier, D. and D. P. Millar (2002). "Energetics of hydrogen bond networks in RNA: hydrogen bonds surrounding G+1 and U42 are the major determinants for the tertiary structure stability of the hairpin ribozyme." *Biochemistry* 41(48): 14095-102. [http://www.ncbi.nlm.nih.gov/entrez/query.fcgi?cmd=Retrieve&db=PubMed&dopt=Citation&list_uids=12450372]

Liao, S. and N. C. Seeman (2004). "Translation of DNA signals into polymer assembly instructions." *Science* 306 (5704): 2072-4. [http://www.ncbi.nlm.nih.gov/entrez/query.fcgi?cmd=Retrieve&db=PubMed&dopt=Citation&list_uids=15604403]

Mao, C., W. Sun, Z. Shen and N. C. Seeman (1999). "A nanomechanical device based on the B-Z transition of DNA." *Nature* 397(6715): 144-6. [http://www.ncbi.nlm.nih.gov/entrez/query.fcgi?cmd=Retrieve&db=PubMed&dopt=Citation&list_uids=9923675]

McKendry, R., J. Zhang, Y. Arntz, T. Strunz, M. Hegner, H. P. Lang, M. K. Bailer, U. Certa, E. Meyer, H. J. Guntherodt and C. Gerber (2002). "Multiple label-free biodetection and quantitative DNA-binding assays on a nanomechanical cantilever array." *Proc Natl Acad Sci USA* 99(15): 9783-8. [http://www.ncbi.nlm.nih.gov/entrez/query.fcgi?cmd=Retrieve&db=PubMed&dopt=Citation&list_uids=12119412]

Nutiu, R. and Y. Li (2004). "Structure-switching signaling aptamers: transducing molecular recognition into fluorescence signaling." *Chemistry* 10(8): 1868-76. [http://www.ncbi.nlm.nih.gov/entrez/query.fcgi?cmd=Retrieve&db=PubMed&dopt=Citation&list_uids=15079825]

Roco, M. C. (2003). "Nanotechnology: convergence with modern biology and medicine." *Curr Opin Biotechnol* 14(3): 337-46. [http://www.ncbi.nlm.nih.gov/entrez/query.fcgi?cmd=Retrieve&db=PubMed&dopt=Citation&list_uids=12849790]

Seeman, N. C. (2003). "Biochemistry and structural DNA nanotechnology: an evolving symbiotic relationship." *Biochemistry* 42(24): 7259-69. [http://www.ncbi.nlm.nih.gov/entrez/query.fcgi?cmd=Retrieve&db=PubMed&dopt=Citation&list_uids=12809482]

Seeman, N. C. (2003). "DNA in a material world." *Nature* 421(6921): 427-31. [http://www.ncbi.nlm.nih.gov/entrez/query.fcgi?cmd=Retrieve&db=PubMed&dopt=Citation&list_uids=12540916]

Stojanovic, M. N. and D. M. Kolpashchikov (2004). "Modular aptameric sensors." *J Am Chem Soc* 126(30): 9266-70. [http://www.ncbi.nlm.nih.gov/entrez/query.fcgi?cmd=Retrieve&db=PubMed&dopt=Citation&list_uids=15281816]

Whitesides, G. M. and M. Boncheva (2002). "Beyond molecules: self-assembly of mesoscopic and macroscopic components." *Proc Natl Acad Sci USA* 99(8): 4769-74. [http://www.ncbi.nlm.nih.gov/entrez/query.fcgi?cmd=Retrieve&db=PubMed&dopt=Citation&list_uids=11959929]

Winfree, E., F. Liu, L. A. Wenzler and N. C. Seeman (1998). "Design and self-assembly of two-dimensional DNA crystals." *Nature* 394(6693): 539-44. [http://www.ncbi.nlm.nih.gov/entrez/query.fcgi?cmd=Retrieve&db=PubMed&dopt=Citation&list_uids=9707114]

Winkler, W. C. and R. R. Breaker (2003). "Genetic control by metabolite-binding riboswitches." *Chembiochem* 4(10): 1024-32. [http://www.ncbi.nlm.nih.gov/entrez/query.fcgi?cmd=Retrieve&db=PubMed&dopt=Citation&list_uids=14523920]

Wu, G., H. Ji, K. Hansen, T. Thundat, R. Datar, R. Cote, M. F. Hagan, A. K. Chakraborty and A. Majumdar (2001). "Origin of nanomechanical cantilever motion generated from biomolecular interactions." *Proc Natl Acad Sci USA* 98(4): 1560-4. [http://www.ncbi.nlm.nih.gov/entrez/query.fcgi?cmd=Retrieve&db=PubMed&dopt=Citation&list_uids=11171990]

Yan, H., X. Zhang, Z. Shen and N. C. Seeman (2002). "A robust DNA mechanical device controlled by hybridization topology." *Nature* 415(6867): 62-5. [http://www.ncbi.nlm.nih.gov/entrez/query.fcgi?cmd=Retrieve&db=PubMed&dopt=Citation&list_uids=11780115]

Zhang, X., H. Yan, Z. Shen and N. C. Seeman (2002). "Paranemic cohesion of topologically-closed DNA molecules." *J Am Chem Soc* 124(44): 12940-1. [http://www.ncbi.nlm.nih.gov/entrez/query.fcgi?cmd=Retrieve&db=PubMed&dopt=Citation&list_uids=12405808]

The foregoing references are hereby incorporated herein by reference.

---

What is claimed is:

1. An RNA complex comprising a target RNA molecule and a monomeric unit comprising an RNA having a binding domain, said binding domain comprising a first helical domain having a first paranemic binding site and a second paranemic binding site, said first helical domain connected to a second helical domain having a first paranemic binding site and a second paranemic binding site, such that said target RNA molecule and said monomeric unit comprising an RNA having a binding domain are adapted to self-assemble paranemically so as to form said RNA complex, said monomeric unit comprising an aptameric portion.

2. An RNA complex according to claim 1 wherein said aptameric portion is adapted to bind a fluorophore.

3. An RNA complex according to claim 1 wherein said monomeric unit comprising an RNA molecule forms paranemic motifs of less than 7 half turns, when bound to target to form said complex.

4. An RNA complex according to claim 1 wherein said monomeric unit comprising an RNA molecule forms paranemic motifs of less than 5 half turns, when bound to target to form said complex.

5. An RNA complex according to claim 1 wherein said monomeric unit is in the form of a loop.

6. An RNA complex according to claim 1 wherein said aptameric portion is adapted to bind a fluorophore, and wherein said aptameric portion is bound to a fluorophore.

7. An RNA complex according to claim 6 wherein said monomeric unit additionally comprises a quantum dot structure.

8. A method of making a self-assembled RNA complex comprising the steps:
   (a) placing in reactive contact
      a. a target RNA;
      b. a monomeric unit comprising an RNA having a binding domain adapted to self-assemble paranemically with said target RNA, and said binding domain comprising an aptameric portion bound to a fluorophore; and
      c. a fluorophore; and
   (b) allowing said monomeric unit comprising an RNA having a binding domain to bind to said target RNA paranemically so as to form said RNA complex whereby the fluorescence of said fluorophore changes from that when not bound to said RNA complex.

9. A method of determining the presence of an analyte through the formation a self-assembled RNA complex, said method comprising the steps:
   (a) placing in reactive contact:
      i. a target RNA;
      ii. a monomeric unit comprising an RNA having a binding domain adapted to self-assemble paranemically with said target RNA, and comprising an aptameric portion bound to a fluorophore; and
      iii. a fluorophore; and
   (b) allowing said monomeric unit comprising an RNA having a binding domain to bind to said target RNA paranemically so as to form said RNA complex whereby said fluorophore becomes bound to said aptameric portion whereby the fluorescence of said fluorophore changes in comparison to that when bound to the uncomplexed monomeric unit comprising an RNA;
   (c) detecting the change in fluorescence of said fluorophore between the uncomplexed and complexed state of said target RNA and said monomeric unit comprising an RNA.

10. A method according to claim 9 wherein said change in fluorescence of said fluorophore is determined by a method selected from the group consisting of steady-state and time-resolved optical techniques including steady-state emission, time-resolved photoluminescence and fluorescence upconversion spectroscopies.

11. A sensor adapted to bind an analyte, said sensor comprising:
   (a) a vessel containing:
      i. a target RNA;
      ii. a monomeric unit comprising an RNA having a binding domain adapted to self-assemble paranemically with said target RNA so as to form an RNA complex, and said binding domain comprising an aptameric portion bound to a fluorophore such that the fluorescence of said fluorophore changes when the monomeric unit comprising an RNA binds to said target RNA; and
   (b) a detector to detect said change in fluorescence of said fluorophore between the uncomplexed and complexed state of said target RNA and said monomeric unit comprising an RNA.

12. An RNA monomeric unit comprising an RNA having a binding domain, said binding domain comprising a first helical domain having a first paranemic binding site and a second paranemic binding site, said first helical domain connected to a second helical domain having a first paranemic binding site and a second paranemic binding site are adapted to self-assemble paranemically so as to form an RNA complex with another RNA, said binding domain of said RNA monomeric unit further comprising an aptameric portion bound to a fluorophore.

* * * * *